(12) United States Patent
Auner

(10) Patent No.: US 7,265,235 B2
(45) Date of Patent: Sep. 4, 2007

(54) METHOD FOR PRODUCING HALOSILANES BY IMPINGING MICROWAVE ENERGY

(75) Inventor: Norbert Auner, Taunus (DE)

(73) Assignee: Wacker Chemie AG, Munich (DE)

( * ) Notice: Subject to any disclaimer, the term of this patent is extended or adjusted under 35 U.S.C. 154(b) by 155 days.

(21) Appl. No.: 10/510,583

(22) PCT Filed: Apr. 15, 2003

(86) PCT No.: PCT/DE03/01270

§ 371 (c)(1),
(2), (4) Date: Oct. 8, 2004

(87) PCT Pub. No.: WO03/087107

PCT Pub. Date: Oct. 23, 2003

(65) Prior Publication Data

US 2005/0143592 A1    Jun. 30, 2005

(30) Foreign Application Priority Data

| Apr. 17, 2002 | (DE) | ................................. 102 17 139 |
| May 23, 2002 | (DE) | ................................. 102 22 728 |
| Jun. 17, 2002 | (DE) | ................................. 102 27 041 |

(51) Int. Cl.
  *C07F 7/04*   (2006.01)
  *C07F 7/08*   (2006.01)
  *C07F 7/16*   (2006.01)
(52) U.S. Cl. ..................... 556/472; 204/157.74
(58) Field of Classification Search ............... 556/472; 204/157.74
See application file for complete search history.

(56) References Cited

U.S. PATENT DOCUMENTS

| 2,380,995 A | 8/1945 | Rochow |
| 2,464,033 A | 3/1949 | Gilliam |
| 5,712,405 A * | 1/1998 | Nakayama et al. ......... 556/472 |
| 5,817,855 A | 10/1998 | Langner et al. |
| 5,847,181 A * | 12/1998 | Nakanishi et al. ......... 556/472 |
| 6,528,674 B1 * | 3/2003 | Lewis et al. ............... 556/472 |

FOREIGN PATENT DOCUMENTS

| CN | 1153138 | * | 7/1997 |
| DE | 195 34 922 C1 | | 2/1997 |
| DE | CN 1153138 | * | 7/1997 |
| DE | 199 48 395 A1 | | 3/2001 |

OTHER PUBLICATIONS

Derwent Abstract corresponding to DE 195 34 922 C1.
Derwent Abstract corresponding to DE 199 48 395 A1.

* cited by examiner

*Primary Examiner*—Thurman K. Page
*Assistant Examiner*—Chukwuma Nwaonicha
(74) *Attorney, Agent, or Firm*—Brooks Kushman P.C.

(57) ABSTRACT

Silanes containing halogen which is bound to silicon are prepared using microwave energy. Silicon is reacted with mixtures of elements or compounds selected from the group consisting of halogen or halogen and organohalogen compounds or halogen and hydrogen or halogen and halogen hydrogen or organohalogen compounds or organohalogen compounds and hydrogen or organohalogen compounds and halogen hydrogen or halogen hydrogen or fluorosilanes and hydrogen, or fluorosilanes and halogen hydrogen or hydrogen containing chlorosilanes and hydrogen or hydrogen containing chlorosilanes and halogen hydrogen or organohalogensilanes and hydrogen or organohalogensilanes and halogen hydrogen or hydro-carbons and halogen hydrocarbons.

19 Claims, No Drawings

METHOD FOR PRODUCING HALOSILANES BY IMPINGING MICROWAVE ENERGY

BACKGROUND OF THE INVENTION

1. Field of the Invention

The present invention relates to a process for preparing silanes containing halogen bonded to silicon.

2. Description of the Related Art

An important representative of the halosilanes is silicon tetrachloride (tetrachlorosilane), which is a water-clear, colorless, readily mobile liquid which has a choking odor and fumes under air. Silicon tetrachloride is used to prepare silicones, silanes and silicic esters, to obtain silicon dioxide, $SiO_2$, and very pure silicon, and for the surface treatment of polymers and metals. A further important representative of the halosilanes is silicon tetrafluoride which can be obtained, for example, by reacting silicon dioxide with alkali metal fluoride and sulfuric acid. Unlike silicon tetrachloride, silicon tetrafluoride is gaseous at room temperature.

A series of very hydrolysis-sensitive halogen substitution products are derived from the silanes and have a similar structure to the alkyl halides, for example the chlorohydrocarbons. For example, the chlorosilanes monochlorosilane and dichlorosilane, and also tetrafluorosilane and the hydrogen-containing fluorosilanes monofluorosilane, difluorosilane and trifluorosilane, are colorless gases, while trichlorosilane and tetrachlorosilane are liquid. Also known are bromosilanes which are obtained, for example, by brominated silanes by means of tin tetrabromide.

Chlorosilanes find use as adhesion promoters, for preparing silylamines and for introducing silicon into organic compounds (silylation). Organochlorosilanes, for example methylchlorosilanes, are of industrial significance for the preparation of silicones. The remaining derivatives of the silanes, which would be formulated in a similar manner to the corresponding carbon compounds, for example silanone, are generally, with the exception of the silanols and siloxanes, so unstable that at best their organically substituted representatives have hitherto become known, for example dimethylsilanone. Since 1981, organic derivatives having Si,Si— and Si,C— double bonds (disilene, silabenzene, methylenesilane) have also become known. However, the stabilities cannot be compared with those of analogous carbon compounds.

It is known that silicon tetrachloride can be prepared by heating a mixture of calcined silica and carbon in a chlorine stream or chlorinating ferrosilicon in the presence of silicon carbide, SiC, at 500-1000° C. Carbon-free generation of silicon tetrachloride is not possible.

Similar processes find use for preparing further halosilanes.

The German patent DE 195 34 922 C1 discloses the use of microwave radiation to prepare trichlorosilane. In this known process, tetrachlorosilane is reduced in a fluidized bed reactor, in which a fluidized bed composed of silicon particles is installed in the reactor, the silicon particles are heated to a temperature of from 300 to 1100° C. by irradiation of microwave radiation into the reactor and tetrachlorosilane- and hydrogen-containing reaction gas is passed through the fluidized bed and reacted with the silicon particles to give a product gas which comprises trichlorosilane.

The German laid-open specification DE 199 48 395 A1 discloses a radiation-heated fluidized bed reactor and a process for preparing highly pure polycrystalline silicon by means of this reactor. The radiation source which finds use is one for thermal radiation, in which case the thermal radiation can be generated with the aid of microwave heating.

SUMMARY OF THE INVENTION

It is an object of the invention to specify a process which can be carried out simply and economically for preparing halosilanes which can be carried out with particularly low energy input.

DETAILED DESCRIPTION OF THE PREFERRED EMBODIMENT(S)

This and other objects are achieved by the present invention, relating to a process for preparing halogen-containing silanes of the general formula (I):

$$R_aH_bSiX_c \qquad (I)$$

where
R is a substituted or unsubstituted alkyl or aryl radical having from 1 to 10 carbon atoms of which one or more may be replaced by —CO—, —CO$_2$—, —O—, —S—, —SO—, —SO$_2$—, —NH— or —NR'—, where R' is a substituted or unsubstituted alkyl radical having from 1 to 20 carbon atoms,
X is fluorine, chlorine or bromine,
a is an integer of 0, 1, 2 or 3,
b is an integer of 0, 1, 2 or 3 and
c is an integer of 1, 2, 3 or 4, with the proviso that the sum of a+b+c=4, characterized in that silicon, under the action of microwave energy, is reacted with mixtures of the elements or compounds selected from the group consisting of halogens; halogens and organohalogen compounds; halogens and hydrogen; halogens and hydrogen halides; organohalogen compounds; organohalogen compounds and hydrogen; organohalogen compounds and hydrogen halide; hydrogen halides; fluorosilanes and hydrogen; fluorosilanes and hydrogen halide; hydrogen-containing chlorosilanes and hydrogen; hydrogen-containing chlorosilanes and hydrogen halides; organohalosilanes and hydrogen; organohalosilanes and hydrogen halides; hydrocarbons and hydrogen halides.

It is possible by the process according to the invention to prepare halosilanes with a particularly low energy input, in contrast to the prior art detailed at the outset. The process according to the invention also has the advantage over the prior art processes that silanes can be prepared with an increased selectivity. In contrast to the processes known hitherto, it is also possible to use silicon in the process according to the invention which is obtained, for example, as waste in silicon crystal pulling or silicon polycrystal preparation for electrovoltaics, or in contaminated form. This has a high cost advantage. The process according to the invention can also proceed preferentially without catalyst, which allows the process to be simplified and costs to be reduced.

In the performance of the process according to the invention, it has been found that the bigger the particle size of the silicon, the better it reacts. Preference is thus given in accordance with the invention to using silicon having a particle size of >70 µm.

Preference is given to using crystalline, especially coarsely crystalline, silicon. It is also possible to use single crystals, for example from waste pieces of wafer. However, this does not rule out that amorphous silicon can also be used. Preference is given to using amorphous silicon in a mixture with crystalline silicon of different degrees of purity, in which case particularly good reaction results have been found.

In a further embodiment of the present invention, silicon is used in conjunction with a catalyst or promoter. Such catalysts and promoters are preferably metals or metal compounds, especially copper.

In another variant, silicon is used in conjunction with a substance which absorbs microwave energy and transfers thermal energy to silicon. This substance may simultaneously act as a catalyst or promoter. An example of such a substance is copper.

Such substances and/or catalysts or promoters allow especially amorphous silicon or silicon having a relatively low particle size, for example below 70 μm, to be reacted.

Therefore, if it is assumed that the reactivity of silicon in the process according to the invention is dependent upon particle sizes, preference is given to working, in the case of higher particle sizes, for example >70 μm, only with silicon, while, at lower particle sizes, appropriate substances are used additionally which promote the reaction (catalysts, promoters, microwave energy-absorbing substances, etc.).

As mentioned, the silicon is contacted for the reaction with a gas atmosphere of the halogen or of the halogen compound, optionally with addition of noble gases, preferably argon. Preference is given to using gas atmospheres of the halogen itself or hydrogen halide compounds, and a chlorine atmosphere is used to prepare silicon tetrachloride. It is also possible to use organohalogen compounds.

So that the inventive reaction proceeds continuously, preference is given to using nonpulsed microwave energy. To generate the desired microwave energy, it is possible to use known microwave ovens. In the case of reactions proceeding exothermically, preference is given to using pulsed microwave energy, especially for initiation.

The performance of the process according to the invention is illustrated hereinbelow with reference to a working example. The process was carried out on the laboratory scale.

In order to be able to use glass apparatus and inert gas methods under ambient pressure, a modified domestic microwave oven was used. The safety cage of the oven was provided with drillholes at three points. These drillholes had a separation of 10 cm, and the middle drillhole was arranged centrally. In order to ensure that the apparatus was always within the active range of the oven, the drillholes formed a line with the exit orifice of the magnetron. The normal rotation of the plate was prevented by using a ceramic tile which did not have any connection to the drive unit.

In order to prevent release of energy into the environment, the three drillholes were each screened with the aid of a 12 cm-long copper tube. The length of the tube corresponded to the wavelength of the frequency of 2450 MHz (about 12 cm) used which is obligatory for this oven. Spacer elements made of laboratory glass enabled connection of customary laboratory equipment.

A Panasonic NN-T251 microwave oven was used which irradiated continuously at reduced power and did not pulse.

In the microwave oven was disposed a U-tube. In the U-tube, a weighed amount of silicon was initially placed on a hollowed-out fireclay brick.

What was used was a charge of crystalline silicon having a purity of 99.99% and a particle size of 70-400 μm. After the evacuation and aeration with an argon atmosphere, $Cl_2$ and/or HCl and/or $CH_3Cl$ was passed through the apparatus. Beforehand, the gas also flowed through a wash bottle of concentrated sulfuric acid or, in the case of methyl chloride, of paraffin oil, and was frozen out after the reaction by means of a cold trap which was cooled preferably to an appropriate temperature in the range from −78° C. to −150° C. or, for example, filled with liquid nitrogen.

After the $Cl_2$ and/or HCl and/or $CH_3Cl$ atmosphere around the silicon had been built up, the microwave oven was switched on with a power of 250 W, and time was allowed for the silicon to react substantially while glowing.

Both in the case of $Cl_2$ and in the case of HCl and $CH_3Cl$, this had happened after approx. 5 min. The $Cl_2$ and/or HCl and/or $CH_3Cl$ was subsequently replaced by argon, and the cold trap was poured out.

In the three cases, the following reactions proceeded:

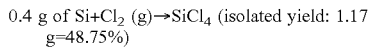
0.4 g of Si+$Cl_2$ (g)→$SiCl_4$ (isolated yield: 1.17 g=48.75%)

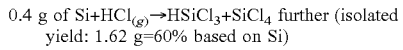
0.4 g of Si+$HCl_{(g)}$→$HSiCl_3$+$SiCl_4$ further (isolated yield: 1.62 g=60% based on Si)

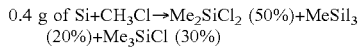
0.4 g of Si+$CH_3Cl$→$Me_2SiCl_2$ (50%)+$MeSiI_3$ (20%)+$Me_3SiCl$ (30%)

Dilution of the methyl chloride or hydrogen chloride gas with argon allows the yield of dimethyldichlorosilane or trichlorosilane to be increased still further:

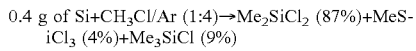
0.4 g of Si+$CH_3Cl$/Ar (1:4)→$Me_2SiCl_2$ (87%)+$MeSiCl_3$ (4%)+$Me_3SiCl$ (9%)

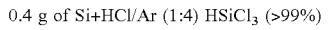
0.4 g of Si+HCl/Ar (1:4) $HSiCl_3$ (>99%)

In addition, a smaller amount of $SiCl_4$ is also detected.

Similarly, the formation of fluorosilanes can also be controlled by the partial argon pressure.

The above-described reaction with methyl chloride provides a novel direct synthesis.

Further halogen compounds which can be used in accordance with the invention are especially unsaturated halohydrocarbons, for example vinyl chloride, allyl chloride, etc., and also the corresponding bromides.

In a further version of the present invention, an alkylation at the silicon can be carried out by the reaction of hydrocarbons, for example methane or ethane, in conjunction with hydrogen halide, for example hydrogen chloride, with silicon under microwave energy input. In a preferred version, methylchlorosilane, for example, is formed in yields of from 5 to 10%.

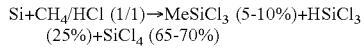
Si+$CH_4$/HCl (1/1)→$MeSiCl_3$ (5-10%)+$HSiCl_3$ (25%)+$SiCl_4$ (65-70%)

For reasons of cost, the silicon used may also be silicon alloys, especially ferrosilicon. Ferrosilicon can have a different Fe content and any particle sizes. This achieves a substantial cost reduction.

The use of, for example, $CH_3Cl$/HCl and $CH_3Cl$/$Cl_2$ and of HCl/$Cl_2$ mixtures, optionally with addition of hydrogen, leads to different SiH-containing products: $MeHSiCl_2$, $MeH_2SiCl$, $H_3SiCl$, $H_2SiCl_2$, $Cl_3SiH$. The addition of $Cl_2$ increases the chlorine content. An increase in HCl leads to a higher SiH content. This also means that the mixing of reaction gases, for example also $H_2C=CHCl$/$CH_3Cl$, $H_2C=CH—CH_2Cl$/$CH_3Cl$ or $H_2C=CH—Cl$, leads to a different organosubstitution on the silicon.

EXAMPLE 98.5% ferro-Si, 1:1 $CH_3Cl$/Ar
$MeSiCl_3$ 6.4%
$Me_2SiCl_2$ 82%
$Me_3SiCl$ 11.6%

Doubling of the Ar amount allows the Me$_2$SiCl$_2$ content to be increased to >90%.

The object specified at the outset is also achieved by the invention in a second process route by a process for preparing compounds of the X$_n$SiH$_{4-n}$ type, where X is halogen and n is 1-3, by contacting mixtures of SiF$_4$ or hydrogen-containing halosilanes, for example hydrogen-containing fluorosilanes or hydrogen-containing chlorosilanes, and hydrogen and/or hydrogen halide gases with elemental silicon under microwave excitation.

Compounds of this type where X is preferably fluorine or chlorine are suitable starting compounds for thermolytically obtaining highly pure silicon which may find use, for example, as semiconductor silicon, for solar cells, photovoltaics, etc. It is synthesized hitherto, for example, by hydrogenating corresponding halosilanes with hydrogenation reagents or by selective comproportionation reactions, in some cases with the aid of suitable catalysts.

An example of a starting material which finds use for the process according to the invention is SiF$_4$. SiF$_4$ can be prepared from low-quality and thus inexpensive Si charges or else from sand/silicates and fluorosilicates. Silicon tetrafluoride can also be prepared, for example, by reacting a silicon dioxide source also of low quality, for example sand, directly with hydrogen fluoride and is thus a possible attractive starting substance for obtaining fluorosilanes.

The purification of these substances by condensation (X=F) or distillation (X=Cl) is easy to carry out.

Although silicon tetrafluoride and tetrachloride are suitable starting materials for obtaining highly pure silicon pyrolytically, the decomposition temperatures are very high (T>>1200° C.) and aggressive gases (fluorine, chlorine) are formed, which leads to corrosion and apparatus problems. For this reason, it is desirable to partially exchange the halogen for hydrogen. The reaction temperatures required to eliminate HX are distinctly lower in comparison to X$_2$ (~700-1400° C.).

It has now been found in accordance with the invention that this partial exchange of halogen for hydrogen by contacting SiF$_4$ or hydrogen-containing halosilanes, for example hydrogen-containing fluorosilanes or hydrogen-containing chlorosilanes, and of hydrogen and/or hydrogen halide gases HX with elemental silicon can be carried out in a simple and economical manner under microwave excitation. In this process, compounds of the X$_3$SiH, X$_2$SiH$_2$ and XSiH$_3$ type where X is preferably Cl, F are prepared. These compounds are suitable silicon precursors, from which highly pure silicon can be obtained by pyrolytic decomposition. Depending on the decomposition temperature, the silicon is obtained in amorphous (T<800° C.) or crystalline (T>1000° C.) form. In the temperature range between approx. 750 and 1000° C., mixtures may also be obtained.

Preference is given to contacting a mixture of the SiF$_4$ or hydrogen-containing halosilanes, for example hydrogen-containing fluorosilanes or hydrogen-containing chlorosilanes, and hydrogen and/or hydrogen halide HX with the elemental silicon. Preference is given to passing this mixture appropriately over the silicon. Further inventive embodiments are the use of fixed bed or fluidized bed reactors.

According to the invention, silicon may also include ferrosilicon having different silicon contents of preferably at least 50%, more preferably 98.5%. The process according to the invention can therefore also be carried out using ferrosilicon.

One advantage of the process according to the invention is that variation of the partial hydrogen pressure, partial hydrogen halide/hydrogen pressure or of the partial halogen/hydrogen pressure allows the average degree of hydrogenation of the products to be regulated. A high H$_2$ or HX concentration leads preferentially to the formation of halosilanes having a high degree of hydrogenation, for example X$_2$SiH$_2$ or XSiH$_3$, whereas a low partial hydrogen or hydrogen halide pressure leads preferentially to the formation of halosilanes having a low degree of hydrogenation, for example X$_3$SiH.

The presence of elemental silicon in the reaction chamber is essential. For example, SiF$_4$ reacts with Si under microwave excitation obviously to give the intermediate difluorosilylene according to the formula SiF$_4$+Si→2F$_2$Si which reacts, for example, with hydrogen primarily to give the dihalosilane F$_2$SiH$_2$. Comproportionation and redistribution, for example F$_2$SiH$_2$+SiF$_4$ SiHF$_3$, result in the mixed fluorosilanes F$_n$SiH$_{4-n}$.

In the case of F$_2$Si, the silylene X$_2$Si resulting from the reaction of SiX$_4$ with silicon is more stable and long-lived than Cl$_2$Si. Subsequent reactions can be controlled more readily. In the course of heating, for example thawing of the matrix (T>35 K), F$_2$Si, unlike Cl$_2$Si, forms a polymeric perfluoropolysilane. This (F$_2$Si)$_x$ forms SiF$_4$ and silicon under pyrolysis conditions (transport reaction)

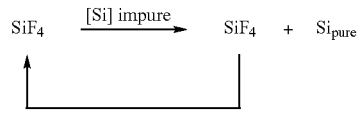

As already mentioned, the inventive reaction may also be carried out using hydrogen halide gas HX as a reaction partner.

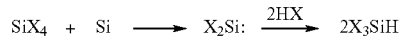

When a mixture of different compounds of the X$_n$SiH$_{4-n}$ type is prepared in the inventive manner, the resulting mixture is preferably separated into the individual compounds or purified by low-temperature distillation (condensation) or liquid distillation. In this case, the resulting mixture is appropriately collected or frozen out in a cooled collecting system, after which the distillation is carried out.

When X$_n$SiH$_{4-n}$ compound or the corresponding compound mixture obtained is decomposed pyrolytically to obtain highly pure silicon, preference is given to introducing the gases formed in the pyrolytic decomposition (halogen X$_2$ or hydrogen halide HX) back into the system for the purposes of a recycling and reusing them directly to synthesize SiX$_4$.

Finally, it should be pointed out that the resulting (X$_n$-SiH$_{4-n}$) mixtures for obtaining Si pyrolytically do not necessarily have to be purified. It is also possible to obtain silicon from the mixture.

What is claimed is:

1. A process for preparing halogen-containing silanes of the general formula (I):

where
R is a substituted or unsubstituted C$_{1-10}$ alkyl or C$_{6-10}$ aryl radical of which one or more carbon atoms are optionally replaced by —CO—, —CO$_2$—, —O—, —S—, —SO—, —SO$_2$—, —NH— or —NR'—, where R' is a substituted or unsubstituted alkyl radical having from 1 to 20 carbon atoms, X is fluorine, chlorine or bromine, a is an integer of 1, 2 or 3, b is an integer of 0, 1, 2 or 3, and c is an integer of 1, 2, or 3, with the proviso that the sum of a+b+c=4, comprising reacting silicon, under the action of microwave energy, with elements or compounds selected from the group consisting of halogens and organohalogen compounds; organohalogen compounds; organohalogen compounds and hydrogen halide; and hydrocarbons and hydrogen halides.

2. The process of claim 1, wherein silicon is contacted with an organohalogen compound, in gaseous form and exposed to microwave energy.

3. The process of claim 1, wherein crystalline silicon is used.

4. The process of claim 1, wherein coarsely crystalline silicon is used.

5. The process of claim 1, wherein amorphous silicon is used.

6. The process of claim 5, wherein amorphous silicon is used in admixture with crystalline silicon.

7. The process of claim 1, further comprising employing a catalyst or promoter.

8. The process of claim 1, further comprising employing a substance which absorbs microwave energy and transfers thermal energy to silicon.

9. The process of claim 1, further comprising employing a metal or metal compound as a catalyst or promoter.

10. The process of claim 9, wherein said promoter comprises Cu.

11. The process of claim 1, wherein nonpulsed microwave energy is used.

12. The process of claim 1, wherein said silicon has a mean particle size of >70 µm.

13. The process of claim 1, wherein said organohalogen compound comprises an alkyl halide or aryl halide.

14. The process of claim 1, wherein said organohalogen compound comprises methyl chloride.

15. The process of claim 1, wherein silicon is employed in the form of a silicon alloy.

16. The process of claim 15, wherein said silicon alloy is ferrosilicon.

17. The process of claim 1, wherein elemental silicon and one or more organohalogen compounds are contacted under microwave excitation with hydrogen, hydrogen halide, or hydrogen and hydrogen halide.

18. The process of claim 1, wherein the hydrocarbon is methane or ethane.

19. The process of claim 1, wherein the silicon is free of catalysts.

* * * * *